United States Patent [19]

Sipila et al.

[11] 4,180,735

[45] Dec. 25, 1979

[54] METHOD AND DEVICE FOR MEASURING THE PARTICLE SIZE IN A SLURRY OR A FLOW OF MATERIAL

[75] Inventors: Heikki J. Sipilä; Seppo J. Uusitalo, both of Espoo, Finland

[73] Assignee: Outokumpu Oy, Helsinki, Finland

[21] Appl. No.: 829,959

[22] Filed: Sep. 1, 1977

[30] Foreign Application Priority Data

Sep. 8, 1976 [FI] Finland ................................. 762578

[51] Int. Cl.² ....................... G01N 23/00; G01N 21/24
[52] U.S. Cl. .................................. 250/358 R; 250/434
[58] Field of Search ............... 250/356, 357, 358, 359, 250/272, 273, 277, 308, 432, 435, 434; 356/102, 167; 324/71 CP

[56] References Cited

U.S. PATENT DOCUMENTS

| | | | |
|---|---|---|---|
| 3,449,567 | 6/1969 | Olivier et al. | 250/357 |
| 3,982,183 | 9/1976 | Collineau et al. | 324/71 CP |
| 4,063,820 | 12/1977 | Borgese | 356/167 |

*Primary Examiner*—Davis L. Willis
*Assistant Examiner*—Janice A. Howell
*Attorney, Agent, or Firm*—Brooks, Haidt, Haffner & Delahunty

[57] ABSTRACT

A method and a device for determining or observing the average particle size or particle size distribution in a flow of material, such as a slurry, wherein the material is allowed to flow at a constant velocity through a radiation beam, the time interval distribution of the radiation quanta passing through the material flow is measured, this distribution describing the particle size distribution and offering a possibility to control any changes in the size distribution, and from the measured time interval distribution is subtracted the known time interval distribution of the quanta of the radiation beam emitted by the source of radiation, this known distribution being a Poisson distribution, and, finally, the particle size or size distribution is determined arithmetically on the basis of the observed change in the time interval distribution. Preferably, the source of radiation is an X-ray tube or a radio isotope source, and the radiation detector may be a scintillation detector, a proportional counter or a semi-conductor detector.

2 Claims, 2 Drawing Figures

METHOD AND DEVICE FOR MEASURING THE PARTICLE SIZE IN A SLURRY OR A FLOW OF MATERIAL

BACKGROUND OF THE INVENTION

1. Field of the Invention

The present invention relates to a method and device for determining or observing the average particle size or the particle size distribution in a slurry or a material flow.

2. Description of the Prior Art

Previously known are various methods for determining the particle size in a slurry or a material flow. It is a known method to direct radiation beams with different energy levels at a slurry and to calculate the average particle size on the basis of the radiation scatter caused by these particles. Also known are various optical methods, and the use of centrifugal force acting on the particles in the flow, for determining the particle size.

SUMMARY OF THE INVENTION

The present invention provides a method of the character once described, which comprises the steps of allowing the material to flow at a constant velocity through a radiation beam, measuring the time interval distribution of the radiation quanta passing through the material flow, this distribution describing the particle size distribution and offering a possibility to control any changes in the size distribution, subtracting from the measured time interval distribution, the known time interval distribution of the quanta of the radiation beam emitted by the source of radiation, which is a Poisson distribution, and determining the particle size or the particle size distribution arithmetically on the basis of the observed change in the time interval distribution.

There is also provided a device for carrying out said method, comprising in combination, a source of radiation, a material flow conveyor, such as a cuvette for causing the material to flow at a constant velocity, limiters for limiting the radiation emitted by the source of radiation to a beam directed through the flow of material, detector means for receiving the radiation quanta passing through the flow, a pulse height analyser or similar device, linked to the detector, for cutting a desired part from the radiation spectrum, a bistable unit linked to the pulse height analyser to deliver to a time-amplitude converter connected thereto beginning and end signals regarding the height limit selected according to the passage of the radiation spectrum, and a single- or multichannel pulse height analyser coupled to the output of the time-amplitude converter to detect the time interval distribution of the radiation quanta and, accordingly, to provide the information about the average particle size or the particle size distribution.

According to the invention it has been observed that the particles present in a slurry or a flow of material cause changes in the time interval distribution of the quanta of a radiation beam passing through the flow. These changes contain the information about the average size and the size distribution of the particles.

Thus, according to the invention a method and device have been obtained for determining and observing the particle size and the particle size distribution, using the time interval distribution of the radiation quanta, and more specifically by observing the effect of the particle flow on the time interval distribution of the radiation quanta. In this case the time interval distribution of the quanta of the source of radiation without "disturbing" particles is assumed as being known or it is measured, as is the flow velocity of the particles.

DESCRIPTION OF THE PREFERRED EMBODIMENT

Figure 1:
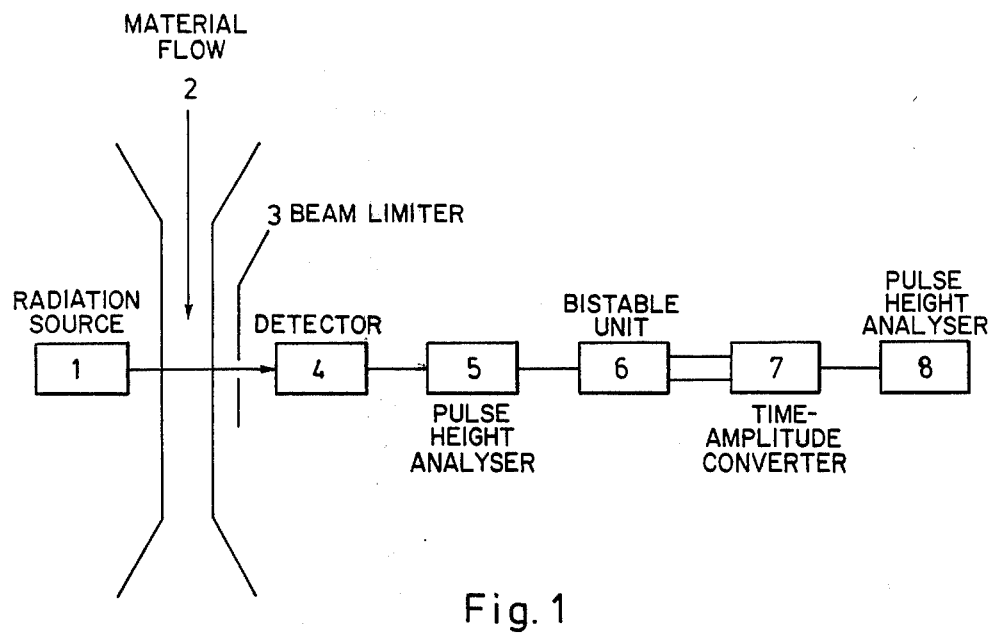
FIG. 1 depicts a block diagram of one embodiment of the device according tho the invention.

FIG. 1 illustrates a device for measuring the particle size. A thin beam of radiation from the source of radiation 1 passes through the particle flow 2 and through limiters 3 to a detector 4. That part of the radiation spectrum which is desired for use is cut by means of a pulse height analyser 5. Beginning and end signals are given alternately to a time-amplitude converter 7 by means of a bistable unit 6. The output of the time-amplitude converter is directed to a single- or multichannel pulse height analyser 8. Information about the average particle size or the particle size distribution is obtained by following the output of this device as described below.

The transmission measurement through a narrow flow cuvette using a thin radiation beam is discussed. (See FIG. 1). Quanta emerge from a constant-efficiency source of radiation 1 in such a manner that their time interval distribution follows the Poisson distribution, i.e.

$$f(t) = (1/\tau)e^{-t/\tau}$$

where $\tau$ is the average pulse interval. When the particles flow through the radiation beam, the original Poisson distribution changes. The changed time interval distribution carries the information about the particle size distribution. This phenomenon is described quantitatively in the following examples.

Figure 2:
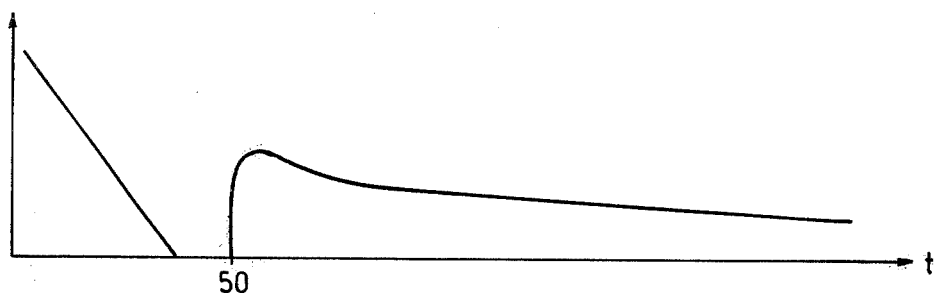
FIGS. 2a, 2b, and 2c depict the time interval distributions of radiation quanta at different passing times of particles.
Figure 2:
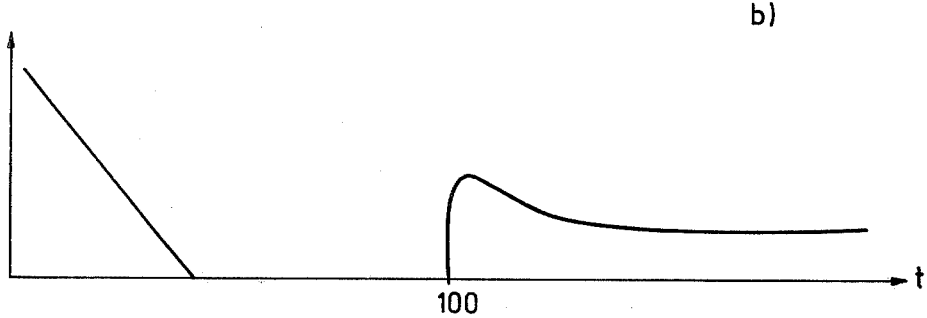
Figure 2:
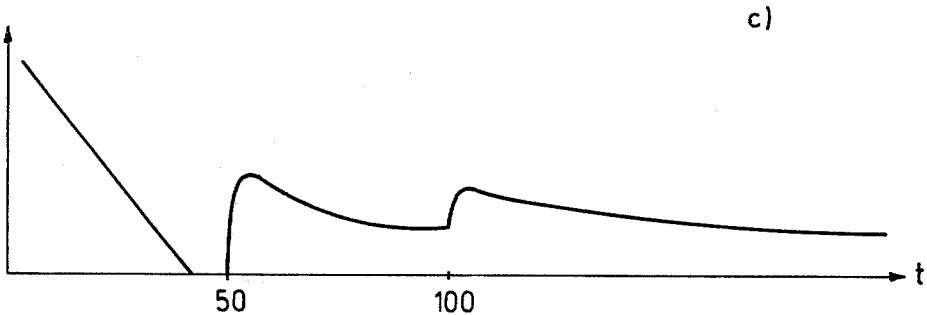

FIG. 2 shows results of simulations performed by the Monte Carlo method. In them the radiation beam has been assumed to be thin and the radiation sufficiently soft so that it is entirely absorbed in the particles. In FIG. 2(a) the particles have a passing time of 50 units, in 2(b) a passing time of 100 units, and in 2(c) 60% of the particles have a passing time of 50 units and 40% one of 100 units. When the flow velocity is standardized, the particle size and the passing time have a direct mutual dependence.

FIG. 2 shows that each particle size gives a certain portion in the time interval distribution outside the Poisson distribution and that in a mixture the portions corresponding to the various components can be added together, weighted by their proportions. The original Poisson distribution is seen on the logarithmic scale as a descending straight line with small time intervals. The shape of the stop for each particle size depends on the density of the particle flow, and consequently its standardization facilitates the treatment of the results. This density can be controlled using the same device. It can be shown analytically that, with the hypotheses of FIG. 2, the following expression is obtained for the average passing time:

$$\tau = (T/S)_o \times (P/M) \times \log(S_o/S),$$

where
T = measuring time
P = number of pulses in Poisson distribution
M = number of pulses outside Poisson distribution
S = total number of pulses
$S_o$ = total number of pulses in the absence of particles.

In this expression log ($S_o$/S) stands for the particle flow density, which can thus be measured by means of the same device.

The average particle size can easily be obtained on the basis of the expression. This is done by classifying the time intervals into those shorter and those longer than a certain limit. The limit is selected so that the shorter time intervals correspond almost solely to time intervals in Poisson distribution (See FIG. 2) and the longer ones to the time intervals caused by particles passing. The number of the former intervals, P, and the number of the latter, M, and S = P+M are placed in the above formula. Taking the flow velocity into account the average particle size is obtained from the passing time $\tau$.

The time interval function is measured in order to measure the size distribution. The proportion corresponding to the Poisson distribution is first subtracted from it arithmetically.

Let the difference be the distribution function g(t). If the distribution function produced by the particle size r is h(r,t) and the proportion of the particle size r in the sample is p(r), $$g(t) = \int_o^\infty p(r) h(r,t) dr$$

is obtained.

The time intervals are classified by multichannel analysis so that the number of pulses $g_i$ is obtained in channel i. The number of pulses $h_{ji}$ given in the channel i by the particle size j is determined by Monte Carlo simulation or experimentally. Thereby the particle sizes have been divided into an equal number of categories as the time intervals. If the proportion of the particle size j in the sample is $P_j$, $$g_i = \sum_j P_j h_{ji}$$

is obtained.

The proportion of each particle size category $P_j$, is obtained using this equation group.

If it is desired only to control that the particle size distribution remains constant, the calculations are not necessary, but that the time interval distribution remains constant is directly controlled.

It is evident that the described embodiment can be varied without deviating from the idea of the invention, i.e., the use of changes in the time interval distribution. If, for example, the source of radiation is sufficiently monoenergetic, the first pulse height analyser can be eliminated. Likewise, for example, the bistable unit can be replaced with a unit which gives a new beginning signal immediately after an end signal.

What is claimed is:

1. A method for determining the particle size distribution in a flow of material which includes particles capable of absorbing X-rays dispersed in a medium through which X-rays pass freely, comprising the steps of causing the material to flow as a thin stream at a constant velocity transversely through a narrow X-ray beam consisting of quanta which are absorbed when such quanta encounter the particles in said stream; limiting the thickness of said stream and limiting the thickness of said beam for generally precluding the presence of several of said particles in said beam at any given time, whereby absorption of quanta generally represents passage of single particles through the beam; measuring the time interval distribution of radiation quanta which have passed through the stream to obtain measurements representing absorption of quanta by particles, which measurements carry information about particle size distribution; subtracting from said measurements the values of a Poisson distribution known to represent the time interval distribution of quanta in the beam prior to passage of the beam through the stream; and determining particle size distribution arithmetically on the basis of the difference in said known and measured time interval distributions.

2. A device for determining the particle size distribution in a flow of material which includes particles capable of absorbing X-rays dispersed in a medium through which X-rays pass freely, comprising in combination, a material flow conveyor for causing the material to flow as a thin stream at a constant velocity, a source of radiation for emitting X-ray radiation consisting of quanta which are absorbed when such quanta encounter the particles in said stream, limiters for limiting the radiation emitted by said source of radiation to a narrow beam directed transversely through said stream of material to generally preclude the presence of several of said particles in said beam at any given time, whereby absorption of quanta generally represents passage of single particles through the beam, X-ray detector means disposed on the other side of said stream from said source of radiation for receiving radiation quanta which have passed through the stream between the passage of particles in the stream and emitting a signal representative of such detected quanta, a pulse height analyser coupled to said detector means for cutting out of said signal a desired part of said signal representing quanta within a selected energy spectrum, a means linked to said pulse height analyser for producing a beginning and an end signal and a new beginning signal immediately after the end signal related to the energy spectrum selected by said pulse height analyser and transmitting said beginning and end signals to a time-amplitude converter, and a further pulse height analyser coupled to the output of said time-amplitude converter for detecting a time interval distribution representative of quanta which have passed through the stream and providing information about the particle size distribution in the flow of material.

* * * * *

UNITED STATES PATENT AND TRADEMARK OFFICE
CERTIFICATE OF CORRECTION

PATENT NO. : 4,180,735
DATED : December 25, 1979
INVENTOR(S) : Sipila et al

It is certified that error appears in the above-identified patent and that said Letters Patent are hereby corrected as shown below:

Column 2, line 67 (last line):

"$\tau = (T/S)_o \times (P/M) \times \log(S_o/S),$" should be

-- $\tau = (T/S_o) \times (P/M) \times \log(S_o/S),$ --.

*Signed and Sealed this*

*Twenty-fifth* Day of *March 1980*

[SEAL]

*Attest:*

SIDNEY A. DIAMOND

*Attesting Officer*    *Commissioner of Patents and Trademarks*